United States Patent [19]

Collins

[11] Patent Number: 4,971,036
[45] Date of Patent: Nov. 20, 1990

[54] VAGINAL SPECULUM

[76] Inventor: Jason H. Collins, 1344 Covington Hwy., Slidell, La. 70460

[21] Appl. No.: 405,775

[22] Filed: Sep. 11, 1989

Related U.S. Application Data

[63] Continuation-in-part of Ser. No. 360,257, Jun. 2, 1989, which is a continuation of Ser. No. 128,635, Dec. 4, 1987, Pat. No. 4,884,559.

[51] Int. Cl.$^5$ .............................................. A61B 1/32
[52] U.S. Cl. ........................................ 128/17; 128/18; 128/3
[58] Field of Search ............... 128/17, 18, 3, 20, 24.1, 128/32, 788, 401; 606/191, 119, 198; 604/77, 21, 281

[56] References Cited

U.S. PATENT DOCUMENTS

| | | | |
|---|---|---|---|
| 268,316 | 11/1882 | Tiptor | 128/708 |
| 659,409 | 10/1900 | Mosher | 128/18 |
| 1,428,653 | 9/1922 | Nick | 128/788 |
| 1,827,306 | 10/1931 | Chapman et al. | 128/788 |
| 1,950,788 | 3/1934 | Ewerhardt | 128/788 |
| 2,483,233 | 9/1949 | Pike | 128/17 |
| 2,672,859 | 3/1954 | Jones | 128/17 |

*Primary Examiner*—Edward M. Coven
*Assistant Examiner*—Mark S. Graham
*Attorney, Agent, or Firm*—Pravel, Gambrell, Hewitt, Kimball & Krieger

[57] ABSTRACT

A vaginal speculum of the type having a first upper blade and second lower blade, the blades moveable in relation to one another via a rear hinge portion, with the ability to be adjustable and used in conjunction with the gynecological procedure, for example, surgery on the cervix. The improvements would include adaptations made to undertake other tests with the vaginal speculum during examination of surgery. These improvements include electrodes built into the distal ends of each of the blade members for blocking the nerve endings of the cervix, the electrodes being utilized in conjunction with a "terms" unit which would have analgesic purposes; a vibration unit adapted to the speculum, for affording muscle relaxation during the examination of the vagina and cervix; a wire filament contained in the edge of the upper and lower blade members for bringing the temperature of the speculum to body temperature for more comfort during use; a pressure gauge providing an indicator on the speculum for recording the pelvic pressures of the patient; a temperature probe at the tip of the speculum to record the temperature of the cervix and vagina; and a chemical strip adapted along the top edge of the upper speculum blade for recording the pH, glucose content, protein content, and otehr chemical results which may indicate early vaginal disorders by the indicators on the chemical strip from the vaginal fluids.

10 Claims, 2 Drawing Sheets

VAGINAL SPECULUM

This application is a continuation-in-part of application Ser. No. 360,257 entitled "Adaptor For Cervical Speculum", filed on June 2, 1989 which is a continuation of U.S. Ser. No. 128,635, filed Dec. 4, 1987, presently pending.

BACKGROUND OF THE INVENTION

1. Field of the Invention

The apparatus of the present invention relates to vaginal speculums. More particularly the present invention relates to an improved vaginal speculum which includes electrodes for blocking the nerve endings at the cervix for relieving pain; a vibrator portion for accommodating muscle relaxation; an element through the speculum blades for heating speculum blades; pressure gauge for checking the pelvic muscle pressures; a temperature probe in the speculum for recording the temperature of the cervix; and a strip member along the outer blade portion of the speculum for recording the pH, glucose content, protein content and other chemical makeup of the vaginal fluid for serving as an early indicator of vaginal disorders.

2. General Background

In the examination of the vagina and cervix, several gynecological examinations must take place in order to obtain a complete record of the patients condition, and whether or not certain disorders that can be found as a result of the tests. In the present state of the art, there is no one instrument that can be utilized for recording certain data following a vaginal or cervical examination, which would be most useful for these type; of examinations. At the present, the single most utilized instrument would be the vaginal speculum, which is utilized to increase the opening of the vagina so that the surgeon has relative easy access to the area being examined or treated. In most of the common speculums, utilized in todays examinations, its comprised of a pair of blade members, the lower blade of which is permanently attached to a handle, and the upper blade of which is positioned parallel wit the lower blade, and is movable between open and closed positions relative to the location of the lower blade so that is the blades are inserted into the vagina the blades may be pulled apart so as to increase the opening of the vaginal to inspect and examine.

In the present state-of-the-art, a vaginal speculum is limited to that particular function, and is really not utilized to accommodate other functions. The only exception, known to Applicant at this time, is Applicants own invention, which is presently under patent pending entitled "Surgical Speculum", bearing U.S. Ser. No. 128,635, filed Dec. 4, 1987 which discloses a modified vaginal speculum having upper and lower lades, the blades moveable in relation to one another, with the blades including tubes on their ends for evacuating smoke and or fluids from the vagina during laser surgery. A second application bearing U.S. Ser. No. 360,257, which is a continuation-in-part of the previous serial number, includes the evacuating tubes which are adhesively adaptable to existing vaginal speculums, and therefore can be utilized in the same manner as the previous invention, but which affords the ability to adapt presently used speculum with the evacuating tubes.

Other patents noteworthy in the art are as follows:

U.S. Pat. No. 2,483,233 issued to Price, et al, entitled "Speculum", relates to a speculum having a tube running in the upper jaw portion for blowing air into or for suctioning off smoke from the vagina following conization or cauterization upon the cervix.

U.S. Pat. No. 2,243,285, issued to Pope, entitled "Operating Scope", which is adapted for positioning of instruments therewithin, the scope adapted with a light source within the walls of the barrel for aspirating fluids therefrom.

U.S. Pat. No. 3,037,505, issued to Walden, entitled "Irrigators Or Spray Devices", relates to a spray device for distribution and injection of medication and cleaning preparations antibody cavities. The invention includes a spray tube which is readily detachable secured to a speculum but the second end of the tube may be coupled to a spring container.

U.S. Pat. No. 3,830,225, issued to Shinnick, entitled "Multi-Purpose Stop Cock Arrangement For Sucking Injection Oxygen Cessory Equipment", relates to a bronchoscope which allows the introduction or removal of fluid or instruments or both without withdrawing the other equipment from the bronchoscope.

Other art pertinent to the present invention is the Stack House Abdominal Smoke Control Valve which is a release system and valve that enables the laser surgeon to evacuate smoke from the inflated abdominal cavity during laser laparoscopy. The apparatus is manufactured and sold by Stack House Associates, Inc., which provides a filtration unit for the by-products from laser surgery of smoke and odor vaporized tissue through the use of a vacuum tube into the area of the laser. Such a filter could be used in conjunction with the present invention.

SUMMARY OF THE PRESENT INVENTION

The apparatus of the present invention offers improvements in vaginal speculums in a simple and straightforward manner. What is provided is a vaginal speculum of the type having a first upper blade and second lower blade, the blades moveable in relation to one another via a rear hinge portion, with the ability) to be adjustable and used in conjunction with the gynecological procedure, for example, surgery on the cervix. The improvements would include adaptations made to undertake other tests with the vaginal speculum during routine examination or surgery. These improvements include electrodes built into the distal ends of each of the blade members, for blocking the nerve endings of the cervix, the electrodes being utilized in conjunction with a "tens"unit which would have analgesic purpose and uses an electrical current; a vibration unit adapted to the speculum. for affording muscle relaxation during the examination of the vagina and cervix (to improve comfort); a wire filament contained in the edge of the upper and lower blade members for bringing the temperature of the speculum to body temperature for more comfort during use; a pressure gauge providing an indicator on the speculum for recording the pelvic pressures of the patient; a temperature probe at the tip of the speculum to record the temperature of the cervix and vagina; and a chemical strip adapted along the top edge of the upper speculum blade for recording the pH, glucose content, protein content, and other chemical results which may indicate early vaginal disorders by the indicators on the chemical strip from the vaginal fluids. Furthermore, each of the blades may be adapted with fluid and smoke evacuator lines, that would enable the speculum to be utilized during laser surgery and evacuate smoke and fluids in the manner as seen in Applicant's earlier application.

Therefore it is the principal object of the present invention to provide a vaginal speculum accommodated with features for undertaking various tests of the cervix and vagina during use;

It is a further object of the present invention to provide a vaginal speculum having the ability to measure the pressure of the pelvic muscles;

It is a further object of the present invention to provide a vaginal speculum having the ability to indicate various chemical components of the vaginal fluid by indications on a chemical strip accommodated on the blade of the speculum;

It is still a further object of the present invention to provide a vaginal speculum having a means for blocking the nerve endings of the cervix, so that pain during or following surgery can be reduced or eliminated;

It is a further object of the present invention to provide a vaginal speculum having a vibration unit for affording muscle relaxation during examination of the patient to provide comfort;

It is a further object of the present invention to provide a heating element on the blades of a vaginal speculum for bringing the temperature of the blades to body temperature;

It is a further object of the present invention to provide a vaginal speculum having a plurality of uses so that the speculum may be utilized to record various vaginal conditions through the use of a single examination tool.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein.

DETAILED DESCRIPTION OF THE PREFERRED EMBODIMENT

Figure 1:
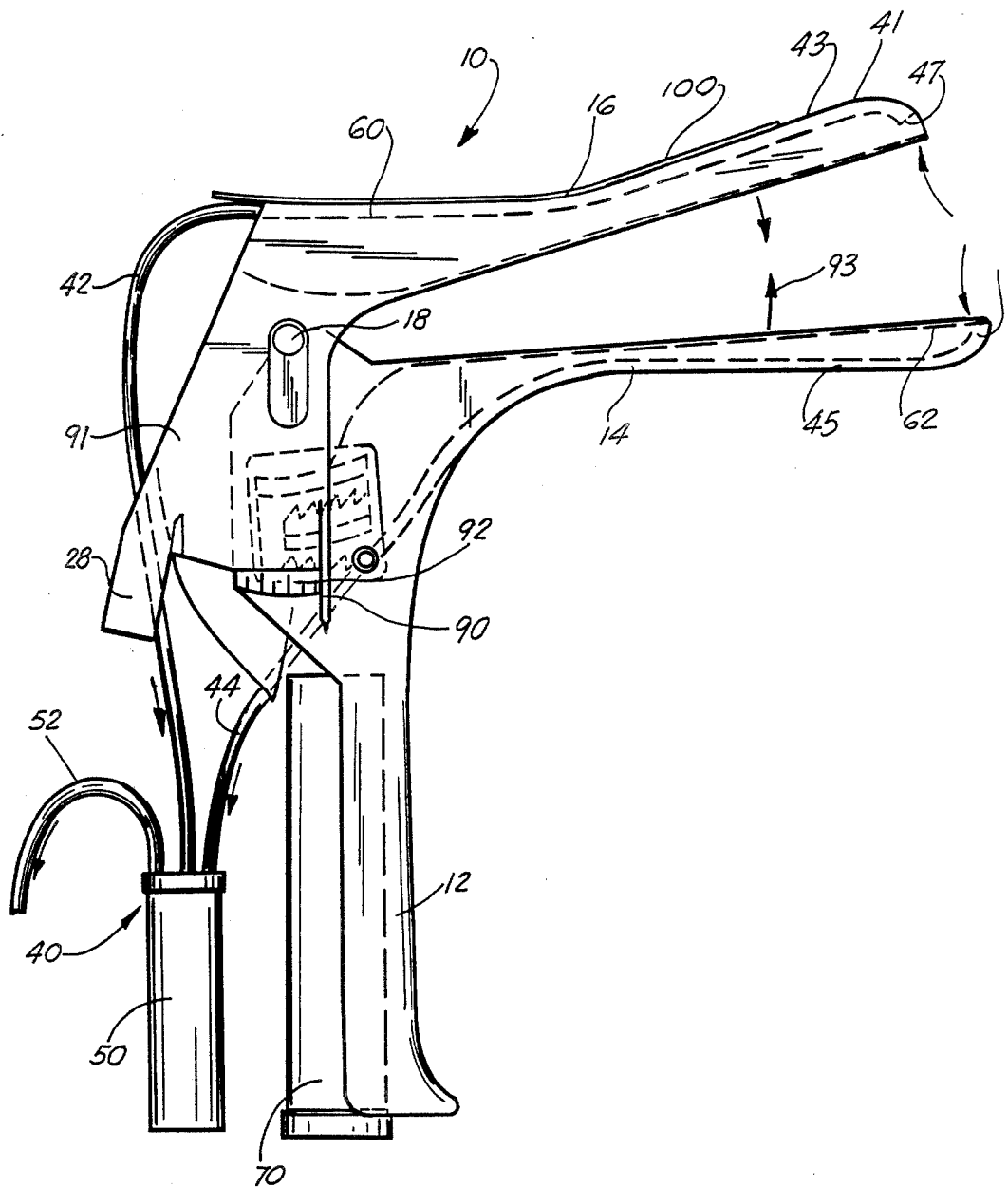
FIG. 1 is a side view of the preferred embodiment of the apparatus of the present invention.

FIGS. 1-4 illustrate the preferred embodiment of the improved speculum of the present invention, as identified by the numeral 10. For purposes of construction as illustrated in FIG. 1, improved speculum 10 would be a typical vaginal speculum of the type having a handle portion 12, a rigid lower jaw member 14 integrally attached to and leading from handle portion 12 and a pivotally supported upward jaw member 16, mounted on a bearing pin 18 at the upper end of handle portion 12 so that the upper jaw 16 is movable between open and closed positions n relation to the fixed jaw 14. In operation, the speculum is used in a normal manner and the jaw 16 is opened away from the fixed jaw 14 to hold the walls of the vagina properly dilated during laser surgery or other examination.

Furthermore, there may be included an adjustment member so that the relative opening between the end portions of blades members 14, 16 may be adjusted for the various openings of a vagina need during examination. Furthermore, there is illustrated a standard thumb handle 28 for effecting the upward and lower movement of blade member 16 during use of the speculum. It should be noted that the blade members 14, 16 are in effect identical and that each of the blade members have an outer convex surface 30 and an inner concave surface 32, for defining a space within the concave surface 32 as illustrated.

Amongst several functions of the new and improved speculum 10, speculum 10 is able to accommodate an adapter which is primarily the subject of the invention in the pending application of the present inventor.

Reference is made to FIG. 1 which illustrates the adapter 40, for evacuating smoke and or fluid from the vaginal cavity during laser surgery. This adapter would include a first upper evacuator tube 42 and a second lower evacuator tube 44. As disclosed in Applicant's previous application, each of the evacuator tubes would be constructed so as to have an upper flattened surface for adhesively attaching to the upper wall 43 and the lower wall 45 of the upper and lower blade member: respectively as illustrated in FIG. 1. Each of the evacuator tubes at their distal end portions 47 would evacuate smoke and fluid through the tubes 42, 44 into a trap 50. The fluid would remain in trap 50 and smoke would then be evacuated out of trap 50 via line 52 to be collected at a distant point. Therefore, this illustrates as with the previous allocation this one feature of the speculum 10, for adapting a "portable" smoke-fluid evacuator system.

Turning now to the additional combinations of the present invention, reference is made to FIG. 1 where there is illustrated a means by which each of the blade members 14, 16 are maintained at body temperature in order to accommodate the patient during use. This means would include filaments 60 and 62 (See F respectively which run along the wall of the blade members 14, 16, which would when activated by an outside source, would heat the blade members 14, 16 to temperatures so that the entire blade members would be at body temperature when ready to be utilized. This outside source can be a battery or the like.

Furthermore, in order to further relieve the possible discomfort in the use of the vaginal speculum on a patient, there would included a means for imparting a vibration to the blade members as they would be inserted into the vagina, so that the muscles of the vagina are relaxed during use. This means would include a vibrating member 70, which may be inserted into the lower handle member 12 of the apparatus, and when activated again to a battery source, would impart vibrations to the entire apparatus and blade members 14, 16 vary slight yet sufficient to cause the muscles of the vagina to relax when the apparatus is being utilized.

Figure 2:
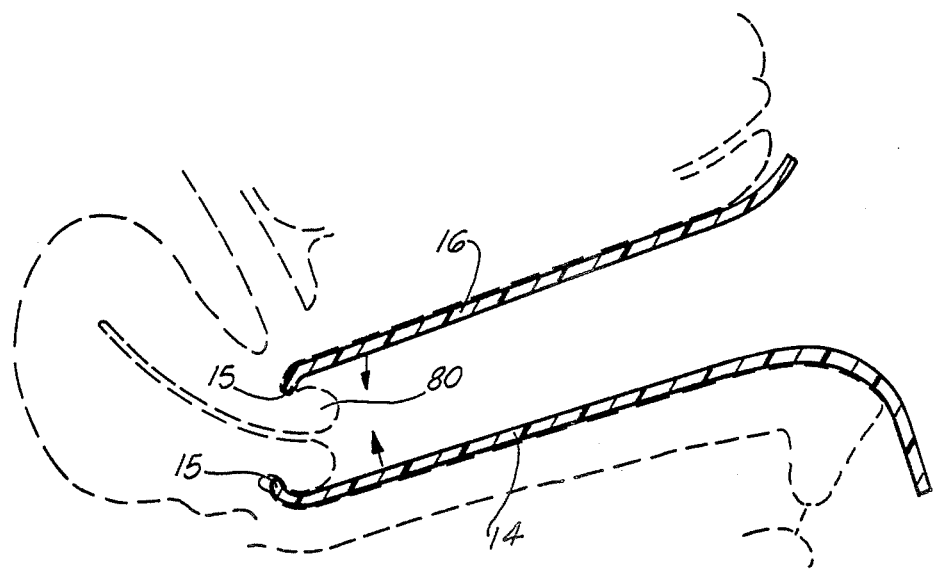
FIG. 2 is a partial side cross-sectional view of the blade members of the present invention placing pressure on the cervix of a patient during examination.
Figure 3:
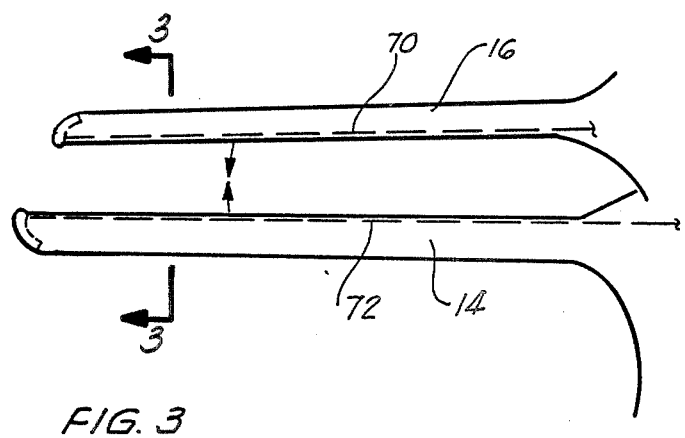
FIG. 3 is a side view of the blade members of the improved vaginal speculum in the closed position.
Figure 4:
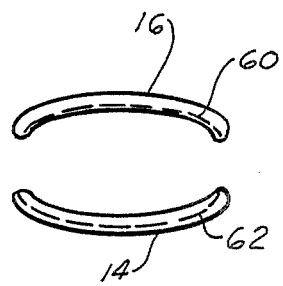
FIG. 4 is a cross-section view of the blade of the vaginal speculum along 3—3 in FIG. 3.

As illustrated in FIGS. 2 and 3. reference is made to an additional inventive combination which would include electrical wires 70, 72 located in the upper blade member 16 and lower blade member 14 respectively. The electrical wires 70, 72 would lead from an apparatus which is known in the art as a "tens" unit, which is in apparatus for relieving pain on the patient through electrical current interrupting the nerve impulses to that particular area. In this use, as illustrated in FIG. 2, there is illustrated the upper blade 16 and lower blade 14 the ends 15 of which are imparting pressure to the cervix 80 of a patient. When the "tens" unit is activated, the electrical current passing through wire 70, 72 would tend to numb the cervix, so that further examination of the cervix and the vagina may be undertaken with reduced or no pain to the patient. The utilization of the "tens" unit in conjunction with the vaginal speculum therefore enable the obstetrician to examine the patient while the cervix is in the numb state particularly in the event that a biopsy or the like is required as part of the examination.

As is further illustrated int he FIGURES, the apparatus would include a means for registering the strength of the muscles int he vaginal walls of a patient. This means would include an indicator 90 located ont he lower base 91 of the upper jaw unit 16, with indicator 90 moving along an indicator graph 92 which is positioned on the base of the lower jaw member 14. In use, the vaginal speculum would be placed within the vagina, and upon the exercise of the muscles of the vagina, the blade of the speculum would be pushed downward to the closed position the direction of arrows 93, and the indicator 90 would register the amount of force on the scale 92. Therefore, this relative measurement could be utilized to indicate the amount of strength that is int he vaginal muscles of a particular patient while being examined.

An additional feature of the apparatus would be the ability of the apparatus when being utilized in examination to record various chemical components within the vaginal fluids, such as the pH of the fluid, the glucose content of the fluid, the protein content of the fluid and other chemical components of the fluid which may be recorded on the strip 100. For purposes of use, the strip 100 would be known as a "chemstrip" which could be adhesively secured to the upper surface 41 of the upper blade 16, with various areas of the strip isolated to record the various chemical components of the fluid. Therefore, as the vaginal speculum is utilized in the examination upon retrieving the speculum, one could simply look at the "chemstrip" and tell from the colonizations of the areas of the "chemstrip" of whether or not various types of chemical components and their relative strengths are contained within the fluid. This would be very useful in diagnosing perhaps a disease or condition in its early stages which in the present state-of-the-art would have to be diagnosed under a completely separate test and could not be achieved in the assembly as is achieved with the present invention.

One of the most important features of the present invention is the fact that the various components such as the evacuation component can be adapted to a present vaginal speculum that is used in the art. Likewise, the "chemstrip" could be adapted to a speculum utilizing the present state-of-the-art, and the vibrating unit 7 could be adapted likewise. Therefore, for the most part the parts to the present invention may be interchangeable and enable a speculum that is utilized presently in the art to be adapted with the features as found in the present invention.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. In a vaginal speculum having an upper blade member, a lower blade member in substantially parallel relationship with the upper blade member, a handle member, so that the upper and lower blade members move between opened and closed positions relative to one another, wherein the improvement comprises:
    (a) a source of electrical current in the end portions of the upper and lower blade members for emitting electrical current to block the nerve endings of the cervix and relieve pain during the examination;
    (b) heating means for bringing the temperature of the upper and lower blade members to norma body temperature during examination;
    (c) means for imparting a slight vibration to the upper and lower blade members to relax muscles of the vagina during examination.

2. The speculum in claim 1, further comprising a chemical strip adhered to one of the blade members for recording the various chemical components within the vaginal fluids.

3. The speculum in claim 1, further comprising means for evacuating fluids and smoke when the speculum is used in conjunction with laser surgery.

4. The speculum in claim 1, wherein the means for imparting electrical current to the nerve endings of the cervix further comprises a "tens" unit.

5. The speculum in claim 1, further comprising a temperature probe at the tip of the speculum for recording the temperature of the cervix during examination.

6. In a vaginal speculum having an upper blade member, a lower blade member; in substantially parallel relationship with the upper blade member, a handle member, so that the upper and lower blade members move between opened and closed positions relative to one another, wherein the improvement comprises:
    (a) means for imparting electrical currents through the cervix for numbing the cervix during examination;
    (b) vibration means for imparting slight vibration to the blade members during vaginal examination;
    (c) means for recording the temperature of the cervix during vaginal examination; and
    (d) evacuator tubes positioned on the upper and lower blade members, each of the tubes establishing a suction for drawing fluids and smoke through the tubes from the vaginal area during laser surgery.

7. In a vaginal speculum having an upper blade member, a lower blade member in substantially parallel relationship with the upper blade member, a handle member, so that the upper and lower blade members move between, opened and closed positions relative to one another, wherein the improvement comprises:
    (a) means for imparting electrical currents through the cervix for numbing the cervix during examination;
    (b) vibration means for imparting slight vibration to the blade members during vaginal examination;
    (c) evacuator tubes positioned on the upper and lower blade members, each of the tubes establishing a suction for drawing fluids and smoke through the tubes from the vaginal area during laser surgery.

8. The speculum in claim 7, further comprising means for recording the temperature of the cervix during vaginal examination.

9. The speculum in claim 7, further comprising means to measure the vaginal muscle strength.

10. The speculum in claim 7, further comprising means to bring the speculum to body temperature prior to examination.

* * * * *